US005700462A

United States Patent [19]

Handelsman et al.

[11] Patent Number: 5,700,462

[45] Date of Patent: Dec. 23, 1997

[54] *BACILLUS CEREUS* STRAIN MS1-9, ATCC 55812

[75] Inventors: Jo Handelsman; Eric V. Stabb; Lynn M. Jacobson; Robert M. Goodman; David W. Johnson; Kevin P. Smith, all of Madison, Wis.

[73] Assignee: Wisconsin Alumni Research Foundation, Madison, Wis.

[21] Appl. No.: 747,477

[22] Filed: Nov. 12, 1996

[51] Int. Cl.$^6$ .......................... A01N 63/00; A01N 63/02; C12N 1/20

[52] U.S. Cl. .................................... 424/93.46; 435/252.5; 504/117

[58] Field of Search ................................ 424/93.46, 93.4; 435/252.31, 252.1, 252.5; 504/117, 121, 123, 353, 327

[56] References Cited

U.S. PATENT DOCUMENTS

| | | | |
|---|---|---|---|
| 4,877,738 | 10/1989 | Handelsman et al. | 424/93.46 |
| 5,543,301 | 8/1996 | Handelsman et al. | 435/34 |
| 5,552,138 | 9/1996 | Handelsman et al. | 424/93.46 |

*Primary Examiner*—Jean C. Witz

*Assistant Examiner*—Susan Hanley

*Attorney, Agent, or Firm*—Quarles & Brady

[57] ABSTRACT

A novel strain of *Bacillus cereus*, designated MS1-9, has been isolated from the environment. The strain MS1-9, ATCC 55812, is one of a number of *B. cereus* strains which are useful as biocontrol agents to combat fungal damping off disease in field crop plants, and strain MS1-9 has exhibited good performance under high disease pressure among a large number of natural isolates in fostering the emergence and growth of alfalfa plants under normal field conditions in the upper midwestern U.S.

3 Claims, No Drawings

*BACILLUS CEREUS* STRAIN MS1-9, ATCC 55812

BACKGROUND OF THE INVENTION

The present invention is in the general field of bacteriology and relates, in particular, to a novel strain of bacteria useful as a biocontrol agent in field applications.

Significant research has been conducted in recent years on the use of biological agents to increase agricultural productivity and efficiency. Biological control based on the use of microorganisms to suppress plant pests or supplement plant growth offers an attractive alternative to chemical pesticides which are less favored than they have previously been because of concerns about human health and environmental quality. Several screening programs have been used before to isolate biological agents which are effective in the laboratory or in the field to combat pests or facilitate plant growth.

An example of a biological control agent into which significant scientific and economic development has occurred is the use of the *Bacillus thuringiensis*. It was recognized that *B. thuringiensis* strains produced toxic proteins which have the ability to specifically kill certain insects and that initial inquiry led to a significant research which has proceeded to identify a large number of *B. thuringiensis* strains having variations and target range in efficacy. In addition, research has been conducted on methods for stabilizing and applying such toxins, or strains harboring them, to a wide variety of field crop situations. It was also discovered that knowledge of *B. thuringiensis* strains was largely transferable to new strains since the toxins required for biological control and methods for preparing inocula for use in the field were generally similar among strains.

Previously it has been found that a specific strain of *Bacillus cereus*, which has been referred to both as UW85 and by its ATCC designation 53522 has biocontrol efficacy in many applications. The UW85 *B. cereus* strain was found to protect alfalfa seedlings from damping off caused by *Phytopthora medicaginis*, tobacco seedlings from *Phytopthora nicotianae*, cucumber fruits from rot caused by *Pythium aphanidermatum*, and peanuts from *Sclerotinia minor*. UW85 is also described, by reference to its ATCC number in U.S. Pat. No. 4,877,738. It was later found that UW85 produced two antifungal compounds which contribute independently to its suppression of damping off fungi due to antifungal and antibacterial activity. The more potent of these compounds, a novel aminopolyol has been designated zwittermicin A while the second compound, not well characterized, was provisionally designated antibiotic B and is now known to be kanosamine.

"Biological control" is defined as pathogen suppression by the use of a second organism. Mechanisms of biological Control are diverse. For example, certain enteric bacteria have been examined for their usefulness in biological control of root rot in alfalfa. It is believed that control is obtained by competition between the enteric bacteria and the fungi for space on the surface of the alfalfa roots. In contrast, a toxin produced by one species of bacteria may be used to control another species of bacteria that appears as a pathogen. Bacterially produced antibiotics are an example of such toxins. The toxin can be isolated from the species producing it and administered directly, as is the common procedure with penicillin, or the species itself may be administered under appropriate circumstances to produce the toxin in situ. Once identified, such toxins produced by soil-dwelling bacteria may have utility in diverse other areas as antifungal or antibiotic agents.

BRIEF SUMMARY OF THE INVENTION

The present invention is summarized in that a novel *Bacillus cereus* strain, here designated MS1-9, ATCC No. 55812, has been isolated from the environment. Strain MS1-9 has been found to have increased efficacy in fostering the growth and establishment of alfalfa plants in field environments of the upper mid-western United States where root rot diseases of alfalfa are severe.

The present invention is further characterized in that a method is described to foster the growth of alfalfa stands by the application of an inoculum including as its active agents a novel *Bacillus cereus* isolate designated MS1-9, ATCC No. 55812.

Other objects, advantages, and features of the present invention will become apparent from the following specification.

DETAILED DESCRIPTION OF THE INVENTION

An original bacterial strain, isolated from soil, exerts biological control over species of fungi responsible for damping off and root rot in plants. This strain is particularly adapted for use in soils having severe alfalfa root rot problems. The strain has been deposited in the American Type Culture Collection, Rockville, Md., on Aug. 30, 1996 and given the designation ATCC 55812, and shall hereinafter be referred to either as Strain MS1-9 or ATCC 55812.

It is further anticipated that certain mutants of MS1-9 also provide biological control comparable to that provided by MS1-9 in severe root rot conditions. These bacterial strains may also be obtained in substantially pure cultures. A "substantially pure" culture shall be deemed a culture of a bacteria, containing no other bacterial species in quantities sufficient to interfere with replication of the culture or to be detectable by normal bacteriological techniques. In addition, it has been discovered that the biological control is exerted principally by means of one or more toxins produced by the bacterial strain.

Strain MS1-9 is one of a group of *Bacillus cereus* strains that are useful biocontrol agents due, at least in part, to the fact that they naturally synthesize antibiotic agents, notably an antibiotic which is the subject of a co-pending patent application. The antibiotic or toxin is found in supernatant fluid and other bacteria-free fluid and culture medium removed from a culture of MS1-9 or of its protecting mutants, has been found to be a "protecting toxin," as that term is defined below. This toxin has been so characterized as to be identifiable independent of its source in cultures of *Bacillus cereus*, and is known and by the coined term "zwittermicin A." Another fraction from the supernatant fluid from a culture of *B. cereus* ATCC 53522 has been found biologically active, having a zoospore lysis capability to zoospores of *Phytopthera medicaginis* (Pmm), but, as revealed below, this zoospore lysis active fraction does not have the antifungal activity of the antibiotic. *Bacillus cereus* antibiotic zwittermicin A has been found to be a highly water soluble molecule of about 396 daltons. The molecule has two amino groups, and is a linear poly-alcohol.

The method by which the biological control referred to in the preceding paragraph may be verified to exist is the "plant protection assay" detailed below. "Biological control" of fungi causing damping off and root rot shall be deemed to exist if, when an effective quantity of MS1-9, its mutants that exhibit biological control, the anti-fungal toxin produced by them, or any other compound or molecule is placed in the soil or other growing medium in the immediate vicinity of the plant to be protected, a statistically significant reduction in the symptoms of damping off or root rot occurs in the presence of one or more pathogens causing these diseases. An "effective quantity" to combat damping off and root rot shall be that quantity sufficient to result in such a visibly significant reduction of symptoms. Clearly, if no quantity of a bacteria or any toxin or other compound is an effective quantity as so defined, that bacteria, toxin, or compound is not capable of exerting biological control over the fungi causing damping off and root rot.

MS1-9 and those of its mutants capable of exerting such biological control shall sometimes be referred to collectively as "protecting" bacteria. *Bacillus cereus* antibiotic and other toxins capable of exerting such biological control shall sometimes be referred to as "protecting" compounds or toxins. Plants, including seeds, seedlings, and mature plants, treated with such an effective quantity of protecting bacteria, their toxins, or *Bacillus cereus* antibiotic shall be referred to as "protected" from root rot or damping off.

The following is a disclosure of the plant protection assay whereby a test material such as a bacteria, a toxin, or the like, may be tested for its ability to exert biological control over a fungus capable of causing the symptoms of damping off or root rot. The seed or seedling of the plant to be protected is planted in a planting medium in the presence of damping off or root rot causing fungi. The planting medium may be a damp soil containing such fungi, vermiculite in water with the fungi present either in the vermiculite and water or in or on the seed or seedling, an agar-based formulation, or any other planting medium in which the seed or seedling will grow and the fungi may freely develop. The bacteria, toxin, or other test material is placed at least in the immediate vicinity of the seed or seedling. Such placement shall be understood to be in the "immediate vicinity" of the seed or seedling if any soluble test material or any soluble exudate of a bacteria being tested will be in actual contact with the germinating seedling.

Preferably, if seed is used, the seed is coated with the test material, and when the test material is so used with respect to a seed, it shall be referred to hereinafter as a "seed inoculum." The process of coating seed with a seed inoculum is generally well known to those skilled in the art, and any conventional method that does not require conditions sufficiently harsh to kill bacteria, to harm the seeds, or to destroy toxins or other materials included in the seed inoculum, is adequate. An easy and preferred method is to apply the bacteria directly to the seed and dry the seed under vacuum.

After a time sufficient for seedling growth and the expression of the symptoms of damping off, seedlings developing from the planted seed may be evaluated for visual evidence of protection, when compared to controls. In strains of alfalfa, soybeans, and snap beans known to be vulnerable to damping off, one to two weeks of growing time in a growth chamber at 24° C. with a 12 hour photoperiod was found to be a period sufficient for the expression of symptoms of damping off when seedlings were being grown in test tubes containing roughly $10^3$ zoospores of Pmm or comparable, damping off-causing fungi. Protected seeds developed into seedlings visually indistinguishable from uninfected seeds while control seedlings developing from unprotected seeds were killed or, in the case of snap beans, exhibited brown lesions on roots and stems, stunted roots, rotted roots, and other visually apparent symptoms of root rot.

Protecting mutants of MS1-9 include both naturally occurring and artificially induced mutants. For example, MS1-9 is generally sensitive to the antibiotics rifampicin and neomycin. However, it is expected that naturally occurring mutants of MS1-9 can be isolated that exhibited resistance to one or the other of these antibiotics. Certain of these mutants, as well as one naturally occurring mutant distinguishable from the parent MS1-9 strain by the appearance of its colonies, will be found to protect alfalfa plants in the plant protection assay. Other mutants of MS1-9 can be artificially induced by subjecting MS1-9 to the mutagen N-methyl-nitrogoguanidine in conventional ways. Similar mutants have been made from other useful *B. cereus* strains, such as UW85 (ATCC 53522), as described in U.S. Pat. No. 4,877,738, the disclosure of which is hereby incorporated by reference.

In terms of conventional bacteriological morphology and colony analysis techniques, strain MS1-9, ATCC 55812, is indistinguishable from UW85, ATCC 53522 or from other useful *B. cereus* biocontrol strains such as AS4-12, ATCC 55609. Strain MS1-9 is sensitive in the P7 phage assay, described below, scores very high on the Erwinia inhibition laboratory assay, also described below, scores high on bioassay, and is positive for the production of both zwittermicin A and the antibiotic formerly referred to as antibiotic B, now known to be kanosamine. The differences between the strains largely relate to the statistical difference in actual field performance conditions, as reported below. The strain MS1-9 has proven to be particularly adapted to those field situations in which alfalfa root rot is especially severe. While on average, over all fields, the performance of strain AS4-12 is better, strain MS1-9 was the only other strain to provide significant and repeatable yield enhancement in fields, such as those in the UW experimental plot at Marshfield, Wisconsin, where alfalfa root rot infestation was severe.

EXAMPLE 1

Origin of Strains

The geographic origins, and physical and chemical characteristics of the soil samples used in this study are listed in Table 1. All samples were taken from the surface horizon. Measurements of soil pH, organic matter, and particle size were made by the University of Wisconsin Soil & Plant Analysis Laboratory (Madison, Wis.).

TABLE 1

Characteristics of soils used in this study

| Soil/Site | Country | pH | % Organic[a] | % Sand, Silt, Clay[b] | Most recent vegetation |
|---|---|---|---|---|---|
| Lutz | Panama | nd[c] | 5.5 | nd | Forest |
| Snyder-Molino | Panama | nd | 6.2 | nd | Forest |
| Barbour-Lathrop | Panama | nd | 7.1 | nd | Forest |
| Moroceli | Honduras | nd | 1.7 | nd | Maize-Beans |
| San Matias | honduras | 5.8 | 1.5 | nd | Maize-Beans |
| LaVega1 | Honduras | 6.3 | 2.3 | nd | Beans |
| LaVega5 | Honduras | 5.9 | 2.5 | nd | Sorghum-Maize |
| Arlington WI | USA | 6.9 | 4.2 | 23, 68, 9 | Alfalfa |
| Hancock WI | USA | 6.6 | 0.8 | 87, 8, 5 | Alfalfa-Oats |
| Marshfield WI | USA | 6.5 | 3.1 | 23, 72, 5 | Alfalfa |
| Lancaster WI | USA | 7.1 | 2.3 | 19, 68, 13 | Alfalfa |
| Madison WI | USA | 7.0 | 3.2 | 27, 56, 17 | Alfalfa |
| Taos NM | USA | 8.1 | 4.3 | nd | Pasture |
| Tifton GA | USA | 6.3 | 1.0 | 87, 12, 1 | Tobacco |
| Douglas Gully | Austrailia | 6.1 | 2.2 | nd | Vineyard |
| Lelystad | Netherlands | 7.5 | 1.8 | 51, 36, 13 | Potatoes |

Isolation and Identification of *B. cereus* Isolates

The bacterial strains and isolates and their origins are listed in Table 2. Bacteria collected from soybean roots were isolated as previously described from plants grown in a field plot in Madison, Wis. (Table 2). The remaining bacteria collected in this study were isolated by placing either an entire alfalfa root or 1 g of soil in a test tube containing 9 ml water and sonicating it for 30 sec. in a Model 2200 bath sonicator (Branson Ultrasonics Corp., Danbury, Conn.). Serial 10-fold dilutions of the suspensions were made in water, and 0.1 ml from dilutions ranging from $10^{-1}$ to $10^{-5}$ were spread on either 1/10-strength trypticase soy agar (1/10-strength TSA) (Becton Dickinson Microbiology Systems, Cockeysville Md.) or MinIC media. Plates were incubated at room temperature or 28° C. for one to three days. The plates containing isolated colonies were used for further study. Colonies that had the morphology typical of *B. cereus* (flat, broad, and cream colored) were picked and streaked for isolated colonies. As a partial selection for *B. cereus*, during either the initial plating or subsequent streak plating, the medium was supplemented with polymyxin (25 µg/ml), cycloheximide (100 µg/ml), and ampicillin (50 µg/ml). All isolates were tested for hemolysis of blood agar, which is diagnostic of *B. cereus*, and those that were non-hemolytic were removed from the collection. Blood agar was obtained from the Wisconsin State Hygiene Lab, Madison, Wis. Isolates were stored on ½-strength trypticase soy agar (½-strength TSA) slants. Alfalfa plants were grown from seed in soil from Arlington Wis. for 21 days in a growth chamber at 24° C. with a 12 hour photoperiod and a light intensity of 244 microeinsteins/$m^2$/s. Soybean plants were grown from seed in a field plot in Madison Wis.

TABLE 2

Strains and isolates used in this study

| Strain(s)/Isolates | Origin |
|---|---|
| ATCC7064, ATCC27877, ATCC12826 | American Type Culture Collection |
| BGSC6A3, BGSC6E1, BGSC6E2, BGSC4A9, BGSC4B1, BGSC4C3, HD1, BGSC4E1, BGSC4F1, BGSC4G1, BGSC4H1, BGSC4I1, BGSC4J1, BGSC4S2 | Bacillus Genetic Stock Center |
| T | U. W. Bacteriology Dept. Collection |
| UW85 | Alfalfa root, Arlington, WI (26) |
| Soy130 | Soybean root, Walnut St. Farm, Madison, WI |
| ALF1, ALF9, ALF10, ALF13, ALF19, ALF23, ALF52, ALF53, ALF79, ALF83, ALF85, ALF94, ALF95, ALF98, ALF99, ALF108, ALF109, AFL115, ALF117, ALF133, ALF137, ALF144, ALF154, ALF157, ALF161, ALF166, ALF167, ALF173 | Roots of alfalfa plants planted in soil from Arlington, WI and grown in growth chamber |
| LUTZ21, LUTZ58, LUTZ128 | Lutz soil |
| SNY14, SNY42, SNY44, SNY45, SNY73 | Snyder-Molino soil |
| BAR78, BAR145, BAR177 | Barbour-Lathrop soil |
| MOR1, MOR28, MOR37 | Moroceli soil |
| SM32, SM43, SM44 | San Matias soil |
| VGA19, VGA118, VGA137 | LaVega1 soil |
| VGA562, VGA577, VGA598 | LaVega5 soil |
| AS7-4, AS8-4, AG8-13, AS4-12, ARL8 | Arlington soil |
| HS1-3, HS23-11, HS24-8, HS2409 | Hancock soil |
| MS1-9, MS3-2, MS8-2 | Marshfield soil |
| LS2-2, LS2-12, LS33-2 | Lancaster soil |
| WS4-12, WS8-8, WS10-15, WS16-4, WS22-12 | Madison soil |
| TNM68, TNM155, TNM243 | Taos soil |
| TG38, TG42, TG126 | Tifton soil |
| DGA34, DGA37, DGA84, DGA94 | Douglas Gully soil |
| LN24, LN75, LN100 | Lelystad soil |

Based on the profiles of fatty acids from 47 isolates analyzed by five Star Labs (Branford Conn.) and Microbial ID (Newark Del.), all of the isolates were classified as members of the *B. cereus* group, which includes the species *B. mycoides*, *B. anthracis* and *B. thuringiensis*. The unique rhizoidal morphology of *B. mycoides* strains differentiates them from *B. cereus*, and none of the isolates in this collection display *B. mycoides*-like morphology. *B. anthracis* is not hemolytic and is usually sensitive to ampicillin and therefore was probably excluded from this collection. Differentiation between *B. cereus* and *B. thuringiensis* is difficult with standard methods. Therefore we have followed current recommendations and considered all isolates gathered in this study as *B. cereus*. Strains BGSC4A9, BGSC4B1, BGSC4C3, HD1, BGSC4E1, BGSC4F1, BGSC4G1, BGSC4H1, BTSC4I1, BGSC4J1 and BGSC4S2 were previously classified by others as *B. thuringiensis*, and that species designation was retained for those strains.

Assay for Sensitivity to Phage P7

The phages P7 (ATCC 75237) and PB were used to help characterize the strains. The susceptibility of *B. cereus* strains to infection by phage P7 has proven to have a strong co-relation to biocontrol utility and antibiotic production. To propagate these phages, we spread a mixture of melted soft agar (4 g agar/l) with approximately $10^6$ PFU of phage and an excess of *B. cereus* strain UW85 on ½-strength TSA plates. Plates were incubated overnight at 28° C. and then the soft agar was scraped off the plates and suspended in ½-strength trypticase soy broth (½-strength TSB), (1 ml/plate). Agar and cells were removed by centrifugation, and the supernatant solution was passed through a 0.2 μm filter. Phage titers were typically $1\times10^{10}$ PFU/ml.

To screen large numbers of isolates for P7 sensitivity, grids of 48 isolates were grown on 1/10-strength TSA and then cells were transferred with a metal replicator onto 1/10-strength TSA plates that had been spread with dilutions of P7 such that they contained approximately $10^8$, $10^4$, and $10^3$ PFU/plate. A 1/10-strength TSA plate containing no phage was used as a control. Isolates that appeared to form patches with decreased growth or plaques on plates containing P7 were tested in the soft-agar overlay assay (described below) to determine if they were $P7^s$. Most isolates that were $P7^r$ in the primary screen were not re-tested.

In the second test for sensitivity of bacterial isolates to P7, each isolate was grown on ½-strength TSA and cells were scraped off plates and mixed in soft agar overlays to form lawns on fresh ½-strength TSA plates. Ten-fold dilutions of P7 were placed in 5-μl drops on the plates, which were then incubated at 28° C. If plaques appeared, the strain was designated P7-sensitive ($P7^s$). Lawns of two isolates, ARL8 and HS23-11, were cleared by undiluted drops of P7, but P7 did not form isolated plaques on these isolates at lower concentrations. The clearing due to high titer drops appeared to be due to P7 rather than a chemical present in UW85 lysates, since high titer drops of lysates of PB, which produces turbid plaques on UW85, did not cause clearing on lawns of ARL8 and HS23-11. Therefore these strains were also scored $P7^s$. Isolates whose lawns appeared unaffected by P7 were scored $P7^r$.

Assay for Inhibition of *Erwinia herbicola*

Inhibition of *E. herbicola* LS005 was assayed as described in Silo-Sub et al. *Appl. Environ. Microbiol.*, 60:2023–2030 (1994), with the following modifications. Three-day-old cultures of each *B. cereus* isolate grown in ½-strength TSB were tested to determine whether they inhibited *E. herbicola* on 1/1000-strength TSA plates. Isolates that produced visible zones of inhibition of *E. herbicola* were tested again. Isolates that produced visible zones of inhibition in both tests were scored $Eh^+$. Isolates that did not noticeably inhibit *E. herbicola* in each of two initial tests were scored $Eh^-$. Some *B. cereus* isolates did not inhibit *E. herbicola* during initial testing but did after storage at −20° C., and certain isolates (ALF115,HD1 and BGSC4S2) had variable phenotypes producing either small zones of inhibition or no zone in subsequent tests; these were classified $Eh^-$.

Assay for Zwittermicin A and Antibiotic B

Zwittermicin A and antibiotic B (kanosamine) were identified in culture supernatants by cation exchange chromatography using CM SEP-PAK cartridges (Millipore, Millford, Mass.) followed by high voltage paper electrophoresis (MVPE). The cation fraction from the equivalent of 4 ml of culture supernatant was applied to the paper, which was stained with silver nitrate after electrophoresis, described in Silo-Suh et al. supra. Isolates that produced material indistinguishable from either authentic zwittermicin A or authentic kanosamine in HVPE were designated zwittermicin A producers or kanosamine producers, respectively. To verify the structural identity of zwittermicin A produced by nine representatives of the collection of isolates, putative-zwittermicin A was purified from these isolates, and subjected to proton nuclear magnetic resonance spectroscopy ($^1$H-NMR) and fast atom bombardment mass spectrometry.

Assay for Suppression of Alfalfa Damping-off

Bacterial isolates were grown for three days in ½-strength TSB and tested in an assay for damping-off. Each isolate was tested on fifteen plants in each of 7 separate experiments with the following exceptions: strain ATCC12826 was omitted from experiments 1 and 2; strain BAR78 was omitted from experiment 4; and strains WS8-8 and LS2-12 were omitted from experiment 5. Statistical analyses (analysis of variance, Dunnet's comparison test, standard error of least squared mean) were conducted using the SAS Computer Program (SAS Institute, Raleigh, N.C.). The data from the seven experiments were pooled and analyzed as a single experiment with seven blocks.

Testing Diversity of Strains

To estimate the diversity of zwittermicin A and kanosamine B-producers, we sought to determine the minimum number of unique zwittermicin A and/or kanosamine B-producing strains in our collection. We considered isolates to be distinct strains only if phenotypic differences between them could be shown. Therefore, isolates were subjected to a series of phenotypic tests. All characterization was performed on isolates that had been colony purified on ½-strength TSA. To test for antibiotic resistance, isolates were streaked on ½-strength TSA containing tetracycline (5 μg/ml), neomycin (5 μg/ml), or chloramphenicol (1 μg/ml), and incubated at 28° C. overnight. Isolates that grew similarly when streaked in the presence or absence of antibiotic were classified as antibiotic resistant to test isolates for pigment production, they were grown on MES minimal medium at 28° C. for seven days and then scored visually. MES minimal medium contained 9.76 g/L 2-[N-morpholine]ethan-sulfonic acid (MES), 2 g/L $(NH_4)_2SO_4$, 0.2 g/L $MgSO_4.7\ H_2O$, 0.25 mg/L $MnSO_4.7\ H_2O$, 1.25 g/L $K_2HPO_4.3H_2O$, 2 g/L L-glutamic acid, 10 mg/L thiamine, 15 g/L agar, 40 mg/L $FeCl_3.6H_2O$, 6 g/L sucrose and 1 mM of the amino acids threonine, serine, leucine, valine, and alanine, and was adjusted to pH 6.1. MES-Thr medium was MES minimal medium lacking threonine. We characterized the ability of isolates to grow on MES-Thr media by streaking isolates onto MES-Thr plates and incubating at 28° C. for four days and recording the rate of appearance of colonies for each strain. Phages ΦATCC 7064 and ΦATCC 27877 were obtained from the American Type Culture Collection and were propagated on bacterial strains ATCC 7064 and ATCC 27877, respectively. Phage Φ63 was propagated on strain Bt-1, and both Φ63 and Bt-1 were obtained from R. Landen. Sensitivity of isolates to phages Φ63, ¢ATCC7064 and ΦATCC27877 was determined by the soft-agar overlay method described above for P7, with plaque formation as the indicator of sensitivity.

Association of Zwittermicin A Production with $P7^s$ and $Eh^+$ Isolates

It was known that *B. cereus* strain UW85 produces two antibiotics, the novel aminopolyol, zwittermicin A, and kanosamine, that contribute to the suppression of alfalfa seedling damping-off. UW85 was originally identified in a labor-intensive screen for biological control activity. The study conducted above was intended to investigate whether sensitivity to P7 ($P7^s$) and the ability to inhibit *E. herbicola* ($Eh^+$) were phenotypes that could be used to identify zwittermicin A producers and useful biocontrol strains.

4,307 *B. cereus* and *B. thuringiensis* isolates were screened for $P7^s$ and/or $Eh^+$ phenotypes. The isolates were obtained from geographically diverse soil samples collected at a total of 16 locations in five countries (Table 1 above), from alfalfa and soybean roots, and from stock culture collections (Table 2 above). The number of $P7^s$ or $P7^rEh^+$ isolates identified from each source and the number of isolates tested was tabulated. $P7^s$ isolates were identified in samples from 14 of the 16 soils examined as well as from alfalfa and soybean roots. Of the 87 $P7^s$ isolates, all were $Eh^+$ except SNY73 and LN100. $P7^rEh^+$ isolates were identified from each of the soils as well as from alfalfa roots. Among all the isolates tested, approximately 2% (85/4,307) of the isolates examined were $P7^sEh^+$and 7% (132/1,876) were $P7^rEh^+$.

Alfalfa Field Stand Studies

Several of the most promising strains were then used as biocontrol inocula in alfalfa fields grown in Arlington, Hancock (Hah), Marshfield (Mar) and West Madison (WM), Wisconsin for the crop years 1993–1995. The results of those field trials are summarized in Tables 3.1, 3.2, 3.3, 4.1, 4.2 and 5 below.

From that data, it was determined that strain AS4-12 had the best overall field performance in most fields in enhancing the stand of alfalfa fields under normal cultivation conditions in the upper midwestern U.S. Also noteworthy, however was the performance of strain MS1-9. MS1-9 gave superior performance at the experimental fields at Marshfield, Wis. These particular fields have an endemic problem with severe rot root diseases of alfalfa, a problem which exhibited itself during this trial. MS1-9 was determined to be one of the best performers from among those screened under severe root rot disease conditions. The beneficial effects from MS1-9 manifested in both increased emergence of alfalfa seedlings as well as increased forage yield.

TABLE 3.1

Comparison of *Bacillus cereus* strains
1993–1994 Alfalfa Field Trials

| | Emergence (plants/m or %) | | | | 1993 First harvest (g/m) | | | |
|---|---|---|---|---|---|---|---|---|
| Treatment | Arl | Han | Mar | WM | Arl | Han | Mar | WM |
| Untreated | 62 | 57.4 | 28 | 73 | 183 | 68 | 191 | 40 |
| Apron | 56 | 77* | 66* | 87* | 261 | 62 | 261 | 24 |
| US85 | 65 | 64 | 32 | 86* | 232 | 80 | 236 | 52 |
| T30 | — | — | — | — | — | — | — | — |
| AP 17-5 | 72 | 44^ | 29 | 68 | 237 | 51^ | 211 | 31 |
| AP 2-1 | 59 | 43^ | 30 | 71 | 206 | 53^ | 221 | 33 |
| AP 4-12 | 89* | 81* | 65* | 96* | 154 | 71 | 288 | 45 |
| AS 23-15 | 58 | 47 | 31 | 81 | 241 | 62 | 218 | 21 |
| HP 20-2 | 53 | 40^ | 31 | 82 | 209 | 52^ | 219 | 36 |
| HP 24-2 | 75* | 54 | 25 | 78 | 305 | 58 | 215 | 42 |
| HS 1-3 | 60 | 47 | 38* | 71 | 240 | 60 | 223 | 38 |
| HS 18-4 | 66 | 62 | 34 | 75 | 221 | 76 | 212 | 41 |
| LP 34-16 | 65 | 55 | 37 | 85 | 311 | 70 | 246 | 23 |
| LP 38-2 | 64 | 52 | 35 | 83 | 349 | 47^ | 229 | 22 |
| LP 4-13 | 63 | 57 | 30 | 76 | 285 | 74 | 218 | 30 |
| LP 15-3 | 60 | 52 | 31 | 74 | 228 | 67 | 203 | 28 |
| MS 1-9 | 61 | 53 | 38* | 82 | 274 | 74 | 250 | 37 |
| MS 19-4 | 52 | 54 | 34 | 70 | 281 | 62 | 233 | 38 |
| WP 27-3 | 63 | 49 | 26 | 85 | 260 | 67 | 219 | 39 |
| WP 36-16 | 63 | 55 | 33 | 75 | 204 | 61 | 226 | 48 |
| WS 12-3 | 75* | 51 | 23 | 64 | 246 | 62 | 186 | 25 |
| WS 12-4 | 68 | 51 | 35 | 75 | 256 | 47^ | 227 | 41 |

*Significantly greater than untreated at P ≦0.10
^Significantly less than untreated at P ≦0.10

Alfalfa cultivar: Iroquois

Soil Types: Arlington; Plano silt loam Mancock; Plainfield loamy sand Marshfield; Withee silt loam West Madison; Plano silt loam

TABLE 3.2

Comparison of *Bacillus cereus* strains
1993–1994 Alfalfa Field Trials

| | 1993 Second harvest (g/m) | | | | 1994 First harvest (g/m) | | | |
|---|---|---|---|---|---|---|---|---|
| Treatment | Arl | Han | Mar | WM | Arl | Han | Mar | WM |
| Untreated | 281 | 151 | — | 253 | 985 | 671 | 731 | 935 |
| Apron | 346 | 137 | — | 256 | 962 | 596 | 826 | 868 |
| UW85 | 367 | 170 | — | 242 | 1117 | 762 | 919 | 924 |
| T30 | — | — | — | — | — | — | — | — |
| AP 17-5 | 325 | 153 | — | 215 | 934 | 642 | 786 | 888 |
| AP 2-1 | 301 | 160 | — | 223 | 920 | 624 | 872 | 940 |
| AS 4-12 | 303 | 154 | — | 248 | 1005 | 635 | 974 | 936 |
| AS 23-15 | 324 | 178 | — | 221 | 1058 | 735 | 847 | 865 |
| HP 20-2 | 302 | 129 | — | 240 | 1141 | 679 | 843 | 933 |
| HP 24-2 | 330 | 155 | — | 223 | 968 | 717 | 817 | 919 |
| HS 1-3 | 337 | 148 | — | 246 | 1008 | 667 | 825 | 931 |
| HS 18-4 | 296 | 161 | — | 230 | 1071 | 654 | 880 | 911 |
| HS 34-16 | 354 | 152 | — | 218 | 1022 | 653 | 884 | 885 |
| LP 38-2 | 434 | 119 | — | 185 | 1012 | 601 | 841 | 912 |
| LP 4-13 | 368 | 161 | — | 197 | 1091 | 684 | 775 | 915 |
| LPP 15-3 | 382 | 166 | — | 229 | 1201 | 654 | 810 | 929 |
| MS 1-9 | 379 | 153 | — | 220 | 1105 | 703 | 949 | 891 |

TABLE 3.2-continued

| Comparison of *Bacillus cereus* strains 1993–1994 Alfalfa Field Trials | | | | | | | | |
|---|---|---|---|---|---|---|---|---|
| | 1993 Second harvest (g/m) | | | | 1994 First harvest (g/m) | | | |
| Treatment | Arl | Han | Mar | WM | Arl | Han | Mar | WM |
| MS 19-4 | 317 | 140 | — | 238 | 938 | 649 | 829 | 929 |
| WP 27-3 | 325 | 145 | — | 231 | 958 | 669 | 727 | 826 |
| WP 36-16 | 298 | 155 | — | 227 | 804 | 651 | 837 | 940 |
| WS 12-3 | 304 | 164 | — | 228 | 1074 | 644 | 780 | 941 |
| WS 12-4 | 373 | 128 | — | 258 | 1066 | 590 | 832 | 921 |

There were no statistically significant differences due to treatment. (α=0.20)

TABLE 3.3

| Comparison of *Bacillus cereus* strains 1993–1994 Alfalfa Field Trials | | | | | | | | |
|---|---|---|---|---|---|---|---|---|
| | 1994 Second harvest (g/m) | | | | Final stand (plants/m or %) | | | |
| Treatment | Arl | Han | Mar | WM | Arl | Han | Mar | WM |
| Untreated | 465 | 479 | 526 | 522 | 28 | 39 | 28 | 45 |
| Apron | 471 | 432 | 632* | 440 | 26 | 53* | 53* | 45 |

TABLE 3.3-continued

| Comparison of *Bacillus cereus* strains 1993–1994 Alfalfa Field Trials | | | | | | | | |
|---|---|---|---|---|---|---|---|---|
| | 1994 Second harvest (g/m) | | | | Final stand (plants/m or %) | | | |
| Treatment | Arl | Han | Mar | WM | Arl | Han | Mar | WM |
| UW85 | 460 | 531 | 557 | 503 | 29 | 45 | 34* | 44 |
| T30 | — | — | — | — | — | — | — | — |
| AP 17-5 | 466 | 478 | 580 | 495 | — | — | — | — |
| AP 2-1 | 459 | 368 | 598* | 521 | — | — | — | — |
| AP 4-12 | 444 | 450 | 678* | 517 | 34 | 56* | 54* | 51 |
| AS 23-15 | 454 | 482 | 452^ | 499 | — | — | — | — |
| HP 20-2 | 480 | 438 | 540 | 530 | — | — | — | — |
| HP 24-2 | 462 | 551 | 550 | 440 | — | — | — | — |
| HS 1-3 | 481 | 431 | 556 | 500 | — | — | — | — |
| HS 18-4 | 428 | 453 | 583 | 466 | — | — | — | — |
| LP 34-16 | 448 | 427 | 577 | 499 | — | — | — | — |
| LP 38-2 | 505 | 423 | 525 | 517 | — | — | — | — |
| LP 4-13 | 447 | 405 | 533 | 463 | — | — | — | — |
| LP 15-3 | 480 | 453 | 551 | 465 | — | — | — | — |
| MS 1-9 | 442 | 475 | 602* | 475 | — | — | — | — |
| MS 19-4 | 500 | 508 | 553 | 419 | — | — | — | — |
| WP 27-3 | 388 | 470 | 562 | 545 | — | — | — | — |
| WP 36-16 | 345 | 463 | 569 | 519 | — | — | — | — |
| WS 12-3 | 483 | 475 | 478 | 498 | — | — | — | — |
| WS 12-4 | 441 | 393 | 521 | 501 | — | — | — | — |

*Significantly greater than untreated P ≦0.2
^Significantly less than untreated

TABLE 4.1

| Comparison of *Bacillus cereus* strains 1994–1995 Alfalfa Field Trials | | | | | | | | | |
|---|---|---|---|---|---|---|---|---|---|
| | Emergence (plants/m or %) | | | 1994 First harvest (g/m) | | | 1994 Second harvest (g/m) | | |
| Treatment | Arl | Han | Mar | Arl | Han # | Mar | Arl | Han # | Mar |
| Untreated | 37 | 27 | 42 | 187 | — | 190 | 356 | — | 426 |
| Apron | 35 | 53* | 79* | 190 | — | — | 291^ | — | — |
| UW85 | 37 | 23 | 51* | 198 | — | 171 | 346 | — | 396 |
| T30 | 38 | 29 | 46 | 176 | — | 187 | 287^ | — | 395 |
| AP 17-5 | 44 | 35* | 47 | 207 | — | 183 | 314^ | — | 374 |
| AP 2-1 | 40 | 36* | 50* | 185 | — | 172 | 304^ | — | 392 |
| AP 4-12 | 29 | 33 | 48 | 148 | — | 192 | 283^ | — | 413 |
| AP 23-15 | 30 | 35* | 50* | 175 | — | 190 | 281^ | — | 389 |
| HP 20-2 | 32 | 35* | 59* | 165 | — | 194 | 250^ | — | 415 |
| HP 24-2 | 34 | 34* | 49 | 188 | — | 205 | 316 | — | 425 |
| HS 1-3 | 34 | 31 | 48 | 115 | — | 198 | 238^ | — | 405 |
| HS 18-4 | 34 | 26 | 52* | 133 | — | 192 | 248^ | — | 451 |
| LP 34-16 | 38 | 32 | 51* | 171 | — | 202 | 239^ | — | 383 |
| LP 38-2 | 35 | 34 | 51* | 159 | — | 192 | 311 | — | 401 |
| LP 4-13 | 31 | 38* | 58* | 181 | — | 212 | 331 | — | 441 |
| LP 15-3 | 35 | 36* | 47 | 173 | — | 183 | 297^ | — | 404 |
| MS 1-9 | 34 | 30 | 50* | 182 | — | 200 | 335 | — | 429 |
| MS 19-4 | 33 | 35* | 51* | 170 | — | 213 | 318 | — | 421 |
| WP 27-3 | 29 | 28 | 55* | 154 | — | 204 | 260^ | — | 441 |
| WP 36-16 | 33 | 28 | 40 | 141 | — | 173 | 249^ | — | 425 |
| WS 12-3 | 32 | 32 | 45 | 166 | — | 195 | 298^ | — | 374 |
| WS 12-4 | 33 | 36* | 53* | 144 | — | 188 | 299^ | — | 365 |

*Significantly greater than untreated control P ≦0.20
^Significantly less than untreated control
The Hancock trial was replanted in the fall of 1994

Alfalfa cultivar: Iroquois
Soil Types: Arlington; Plano silt loam Hancock; Plainfield loamy sand Marshfield; Withee silt loam

TABLE 4.2

Comparison of *Bacillus cereus* strains
1994–1995 Alfalfa Field Trials

| | 1995 First harvest (g/m) | | | 1995 Second harvest (g/m) | | | Final Stand (Plants/m or %) | | |
|---|---|---|---|---|---|---|---|---|---|
| Treatment | Arl | Han | Mar | Arl | Han # | Mar | Arl | Han # | Mar |
| Untreated | 688 | 529 | 1346 | 563 | 715 | 493 | 27.6 | 30.8 | 41.0 |
| Apron | 774 | 651 | 1109 | 571 | 861 | 432 | 27.8 | 49.6* | 68.4* |
| UW85 | 774 | 573 | 1272 | 508 | 670 | 496 | 29.2 | 26.2 | 51.2* |
| T30 | 767 | 630 | 1122 | 551 | 840 | 446 | — | — | — |
| AP 17-5 | 828 | 629 | 1247 | 559 | 770 | 456 | — | — | — |
| AP 2-1 | 751 | 622 | 1256 | 426 | 809 | 506 | — | — | — |
| AP 4-12 | 747 | 630 | 1195 | 517 | 806 | 437 | 22.4 | 38.4 | 53.0** |
| AP 23-15 | 832 | 644 | 1200 | 505 | 859 | 431 | — | — | — |
| HP 20-2 | 720 | 574 | 1418 | 512 | 796 | 522 | — | — | — |
| HP 24-2 | 793 | 638 | 1383 | 525 | 832 | 484 | — | — | — |
| HS 1-3 | 777 | 571 | 1174 | 482 | 761 | 464 | — | — | — |
| HS 18-4 | 725 | 538 | 1295 | 524 | 709 | 411 | — | — | — |
| LP 34-16 | 822 | 680 | 1218 | 472 | 764 | 450 | — | — | — |
| LP 38-2 | 951 | 617 | 1111 | 542 | 810 | 460 | — | — | — |
| LP 4-13 | 667 | 676 | 1375 | 501 | 742 | 483 | — | — | — |
| LP 15-3 | 741 | 645 | 1202 | 514 | 839 | 456 | — | — | — |
| MS 1-9 | 729 | 548 | 1269 | 582 | 756 | 468 | — | — | — |
| MS 19-4 | 842 | 566 | 1278 | 557 | 796 | 488 | — | — | — |
| WP 27-3 | 688 | 604 | 1255 | 447 | 765 | 443 | — | — | — |
| WP 36-16 | 822 | 554 | 1259 | 581 | 806 | 464 | — | — | — |
| WS 12-3 | 856 | 604 | 1132 | 542 | 789 | 447 | — | — | — |
| WS 12-4 | 769 | 656 | 1140 | 510 | 763 | 406 | — | — | — |

The Hancock trial was replanted in the fall of 1994.

TABLE 5

Comparison of *Bacillus cereus* strains
1995 Alfalfa Field Trials
Establishment year

| | Emergence (plants per meter of row) | | | First harvest (fresh weight in grams) | | | Second harvest (fresh weight in grams) | | |
|---|---|---|---|---|---|---|---|---|---|
| Treatment | Arl | Han | Mar | Arl | Han # | Mar | Arl | Han # | Mar |
| Untreated | 32 | 35 | 62 | — | 403 | 301 | 512 | 636 | 1065 |
| Apron | 34 | 57* | 72 | — | 516 | 310 | 456 | 750 | 1037 |
| Kodiak | 36 | 33 | 75 | — | 378 | 289 | 426 | 611 | 970 |
| UW 85 | 22 | 37 | 86 | — | 496 | 285 | 509 | 704 | 972 |
| T 30 | 44 | 44 | 78 | — | 523 | 283 | 533 | 789 | 945 |
| AS 4-12 | 39 | 44 | 62 | — | 459 | 314 | 524 | 779 | 1003 |
| HP 20-2 | 18 | 38 | 67 | — | 437 | 297 | 349 | 717 | 1025 |
| HP 24-2 | 33 | 30 | 67 | — | 363 | 293 | 449 | 655 | 928 |
| LP 4-13 | 26 | 40 | 75 | — | 415 | 319 | 482 | 696 | 989 |
| MS 1-9 | 28 | 44 | 86 | — | 560 | 291 | 390 | 770 | 1002 |

*Significantly greater than the untreated control (P ≦0.2)
^Significantly less than the untreated control
The Hancock trial was replanted in the fall of 1994
— Not collected due to severe leafhopper damage Alfalfa cultivar: Magnum III
Soil Types: Arlington; Plano silt loam Hancock; Plainfield loamy sand Marshfield; Withee silt loam

We claim:

1. A biologically pure culture of a bacteria having the identifying characteristics of *Bacillus cereus* MS1-9, ATCC 55812.

2. An inoculum for application to alfalfa comprising a carrier and an effective quantity of a bacteria having the identifying characteristics of *Bacillus cereus* MS1-9, ATCC 55812.

3. A method for protecting alfalfa in a growing medium from damping off disease comprising the steps of placing in the vicinity of the plant to be protected an effective quantity of a bacteria having the identifying charateristics of *Bacillus cereus* MS1-9, ATCC 55812.

* * * * *

UNITED STATES PATENT AND TRADEMARK OFFICE

CERTIFICATE OF CORRECTION

PATENT NO. : 5,700,462

DATED : December 23, 1997

INVENTOR(S) : Handelsman, et al

It is certified that error appears in the above-identified patent and that said Letters Patent is hereby corrected as shown below:

In column 1, please insert the following text after the title:

--STATEMENT REGARDING FEDERALLY SPONSORED RESEARCH

This invention was made with United States government support awarded by USDA, Grant # USDA Hatch No. 3553; and AGRICCREE award No. 92-34103-7170. The United States government has certain rights in this invention.--

Signed and Sealed this

Twenty-eighth Day of April, 1998

Attest:

BRUCE LEHMAN

Attesting Officer

Commissioner of Patents and Trademarks